(12) United States Patent
Sharp

(10) Patent No.: US 7,637,261 B2
(45) Date of Patent: Dec. 29, 2009

(54) SLEEP APNEA TREATMENT DEVICE AND METHOD

(76) Inventor: Michael C. Sharp, 184 Lystra Estates Dr., Chapel Hill, NC (US) 27517

(*) Notice: Subject to any disclaimer, the term of this patent is extended or adjusted under 35 U.S.C. 154(b) by 179 days.

(21) Appl. No.: 11/301,157

(22) Filed: Dec. 12, 2005

(65) Prior Publication Data

US 2007/0131231 A1 Jun. 14, 2007

(51) Int. Cl.
A61F 5/56 (2006.01)
(52) U.S. Cl. .................................... 128/848
(58) Field of Classification Search ............... 128/848
See application file for complete search history.

(56) References Cited

U.S. PATENT DOCUMENTS

| | | | | |
|---|---|---|---|---|
| 4,339,151 A | * | 7/1982 | Riggs | 297/464 |
| 4,560,201 A | * | 12/1985 | Scott | 297/393 |
| 4,804,351 A | * | 2/1989 | Raml et al. | 450/58 |
| 4,816,005 A | * | 3/1989 | Braaten | 450/58 |
| 5,509,869 A | * | 4/1996 | Miller | 482/10 |
| 5,787,894 A | * | 8/1998 | Holt | 128/848 |
| 5,893,365 A | * | 4/1999 | Anderson | 128/848 |
| 6,098,856 A | * | 8/2000 | Reilly | 224/160 |
| 7,004,545 B2 | * | 2/2006 | Miller | 297/393 |
| 7,032,597 B1 | * | 4/2006 | Frank | 128/846 |
| 7,124,758 B1 | * | 10/2006 | Frank | 128/848 |

* cited by examiner

Primary Examiner—Patricia M Bianco
Assistant Examiner—Camtu T Nguyen
(74) Attorney, Agent, or Firm—Olive & Olive, P.A.

(57) ABSTRACT

A device and method to be used in treating sleep apnea comprising a headband adapted by reason of its size and shape to fit around a person's head, a garment adapted to being secured to the torso portion of a person using the device consisting of a front section and a back section, a first strap affixed at an upper end to a location on the headband, a second strap affixed at an upper end to a second location on the headband, and wherein the first and second straps are affixed at their lower ends to the back section of the garment so as to provide sufficient tension in the straps to cause the person's head to be tilted backwards thereby opening the person's airway.

12 Claims, 4 Drawing Sheets

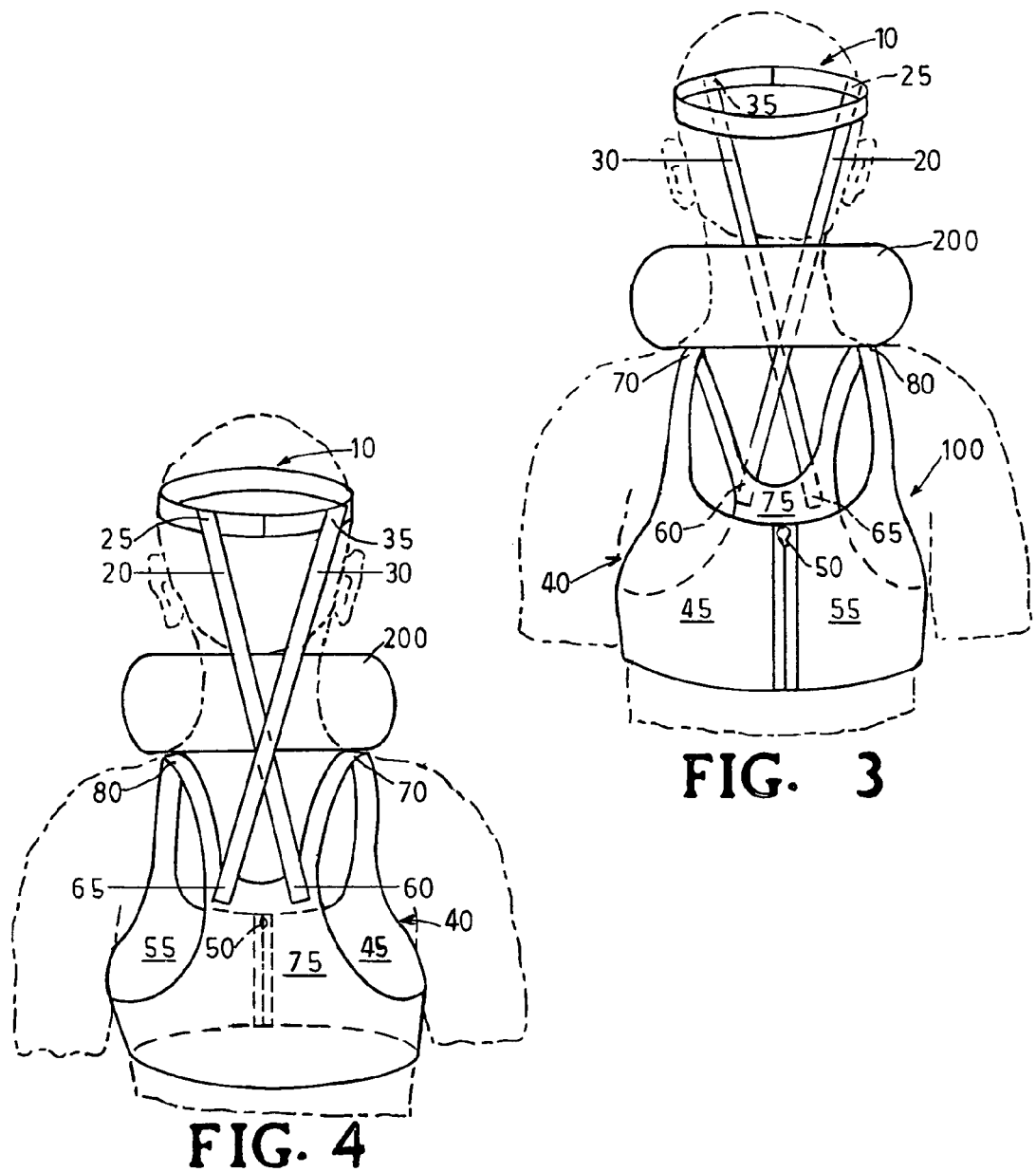
FIG. 3
FIG. 4
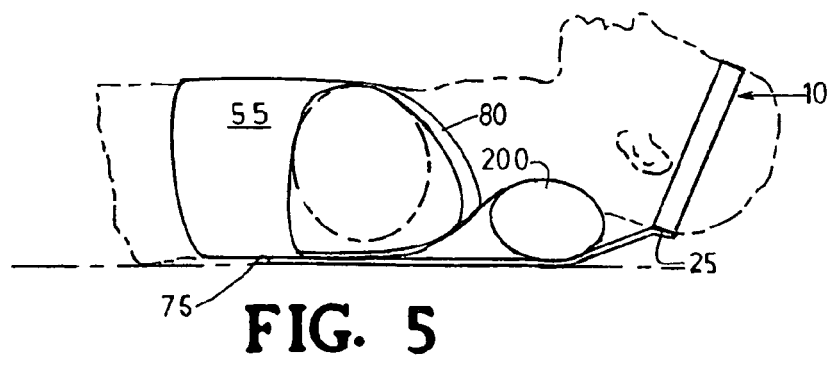
FIG. 5

SLEEP APNEA TREATMENT DEVICE AND METHOD

SUMMARY OF THE INVENTION

Sleep apnea is a relatively common sleeping disorder caused by a variety of different conditions. The most common kind of sleep apnea is obstructive sleep apnea caused by an obstruction of the airway by narrowing or collapse of the tissues in the posterior pharynx to a critical degree. Almost all patients with obstructive sleep apnea are either overweight or regular snorers and the disorder is more common as people get older. Sleep apnea can cause excessive fatigue and poor mental performance during waking hours. There is also considerable strain on the heart. If the disease is untreated it can cause both heart failure and a disease known as pulmonary hypertension.

The diagnosis of the disorder is somewhat problematic. Insurance companies will often only pay for and accept a diagnosis made by a sleep study performed in a sleep laboratory and often will only pay for treatment of individuals confirmed by such a study to have the condition. Most studies are equivocal. Patients are often reluctant to pay for the treatment out of pocket because of the uncertainty of the diagnosis and the cost of the treatment.

A commonly used therapy for sleep apnea is Continuous Positive Airway Pressure (CPAP). Other forms of therapy are considered either risky and expensive, such as various forms of palatal surgery, or inexpensive and ineffective, such as mouth guards. CPAP is typically not considered to be risky but it can be expensive and uncomfortable. Treatment may involve wearing a tight fitting mask that covers the nose.

The present invention provides a much simpler technique to treat sleep apnea than those mentioned above by providing a device which in use tends to open the airway in a person by causing them to tilt their head backwards. This changes the angle of the tongue, oral-nasal-pharynx and trachea such that a normally narrow passageway becomes more open.

BRIEF DESCRIPTION OF THE DRAWINGS

FIG. 3 is a front perspective view of the device of FIG. 1 worn by a person and with a neck support pillow in use.

FIG. 4 is a rear perspective view of the device of FIG. 1 worn by a person and with a neck support pillow in place.

FIG. 5 is a side perspective view of the device as depicted in FIGS. 1 and 2 worn by a person, with a neck support pillow in place, and the person in a lying down or sleeping position.

DETAILED DESCRIPTION

Figure 1:
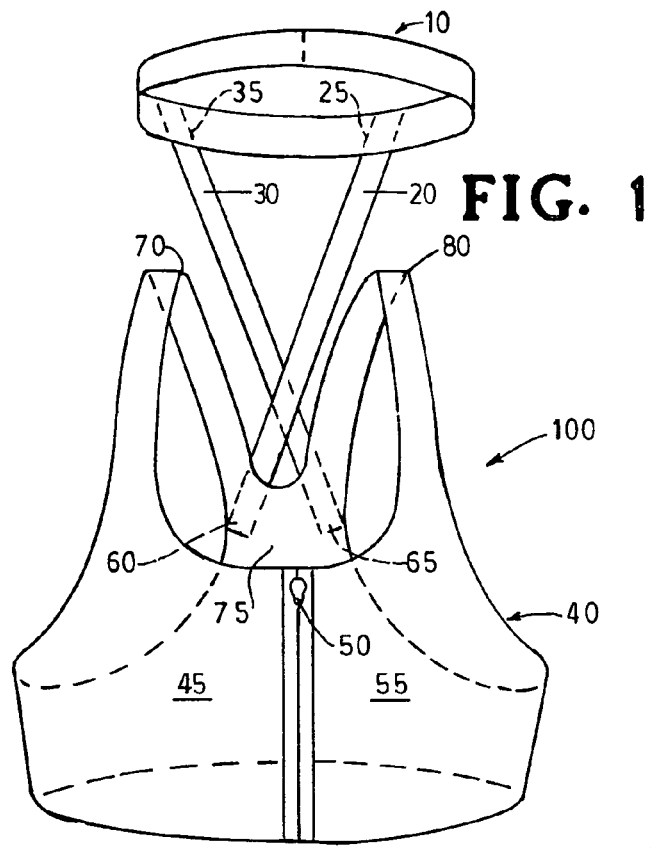
FIG. 1 is a front perspective view of the sleep apnea treatment device according to a first embodiment of the invention.
Figure 2:
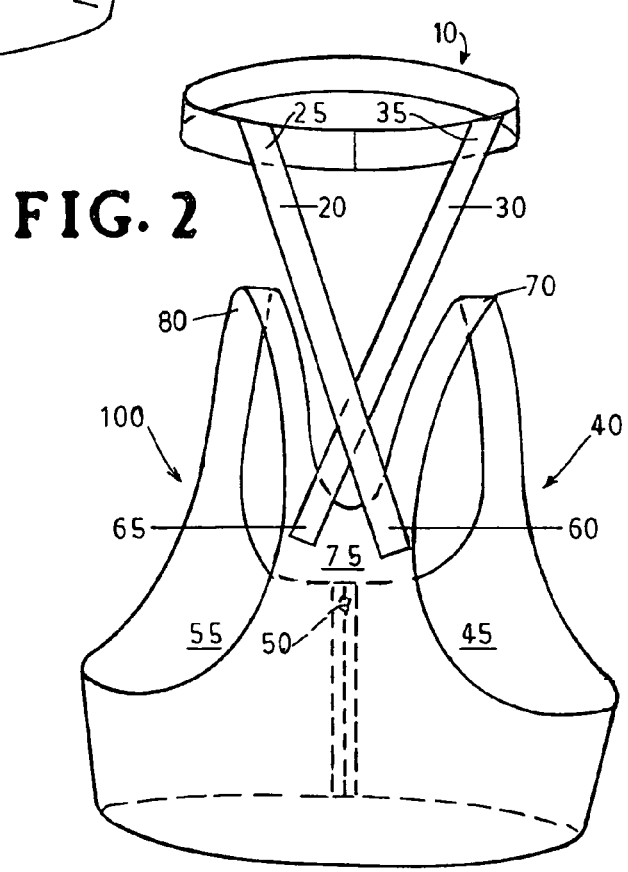
FIG. 2 is a rear perspective view of the sleep apnea treatment device of FIG. 1.

The preferred and first embodiment of sleep apnea treatment device 100 is shown in FIGS. 1 and 2 viewing the device from the front and rear respectively. Elastic headband 10 is placed around the head of the user. The upper ends of elastic head straps 20 and 30 are attached to headband 10 at respective laterally spaced locations 25 and 35. Alternative locations on head band 10 are envisioned for attachment of the upper ends of head straps 20 and 30. Such alternate locations for attachment of the upper ends of head straps 20 and 30 may, for example, include locations which are opposite each other. Vest-like garment 40 is composed of a stretchable first front section 45 on the left front side and a stretchable second front section 55 on the right front side of the garment. The first and second front sections 45 and 55 are joined to a stretchable back section 75 and are fastened together in the front of garment 40 by fastener 50, which in the preferred embodiment is a zipper. Alternative front and back sections may include garments made with non-stretchable material. Alternative fasteners to combine the front edges of the two front sections can include hook and loop systems such as Velcro™ as well as other fasteners such as buttons, adjustable buckle and strap arrangements, traditional hook and loop systems, snaps and any other fastening systems that can be used to join two sections of material. In the preferred first embodiment, garment 40 includes shoulder straps 70 and 80 which assist in securing and supporting garment 40 on the person.

Referring to FIGS. 1 and 2, back section 75 of garment 40 is used to anchor the lower ends of head straps 20 and 30 at locations 60 and 65 respectively. Alternatives to elastic head straps 20 and 30 can, for example, be inelastic head straps that are made to size for the user or head straps that are adjustable in length to a degree sufficient to apply tension to tilt the head of the user backwards. Examples of adjustability for such alternative head straps can include the use of a buckle and strap system, hook and loop systems such as Velcro™, buttons, traditional hook and loop systems, snaps and any other means allowing for the head straps to be adjustable in length. By anchoring head straps 20 and 30 to garment 40 as in FIGS. 1 and 2, head straps 20 and 30 provide tension to the back of a user's head, thus tilting the head backwards and opening up the user's airway (See FIG. 5). Alternatives to headband 10 may also include, for example, any head covering such as a hat, a cap or the like that provides anchoring points on the head of the user for the upper ends of head straps 20 and 30. In the preferred first embodiment as shown in FIGS. 1 and 2, head straps 20 and 30 are attached to garment 40 in a criss-cross manner. Alternative embodiments include attachment of head straps 20 and 30 in a non criss-cross manner.

FIG. 3 is a front perspective view of device 100 of FIGS. 1 and 2 and FIG. 4 is a rear perspective view of device 100 worn by a person with a neck support pillow 200 which can be accommodated between straps 20 and 30 and the neck of the person using the device. FIG. 5 is a side perspective view showing the invention device worn by a person and with the neck support pillow 200 in place. The wearer in FIG. 5 is assumed to be in a lying down or sleep position and with the wearer's head tilted back in accordance with effects of the device of the present invention. The use of a neck support pillow 200 provides a vector force giving a slight thrust forward of the upper neck and head-neck joint. This action not only tilts the head back but also assists in pulling the jaw forward slightly. This further opens the airway similar to the action performed in cardiopulmonary resuscitation (i.e., "CPR"). The device 100 with the addition of a neck support pillow 200 provides the same dynamic, as in CPR, by having the straps pass over the neck pillow. The pillows width creates an angle in the strap which pushes the pillow forward and transfers the force to push the neck forward. This would have a similar overall effect as pulling the jaw forward in CPR.

Figure 6:
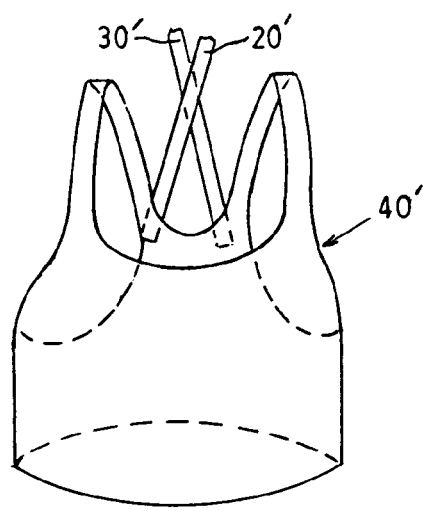
FIG. 6 is a front perspective view showing the body portion formed as a one-piece garment, i.e. without a zipper, according to a second embodiment of the invention.

FIG. 6 is a front perspective view showing in a second embodiment of the invention the body portion 40' formed as a one-piece garment, without fastener 50. Alternative embodiments of garment 40' (not shown) can include any type of bra, bra-like garment, vest or other shirt type clothing as well as garments that do not include shoulder straps (i.e., shoulder straps 70 and 80 as seen in FIGS. 1 and 2). Head straps 20' and 30' (FIG. 6) can, for example, be fastened to the back of any of the indicated alternative embodiments of garment 40' by a variety of means including sewing, hook and loop systems such as Velcro™, buttons, adjustable buckle and strap arrangements, traditional hook and loop systems, snaps and any other fastening systems that can be used to join two pieces of material.

Figure 7:
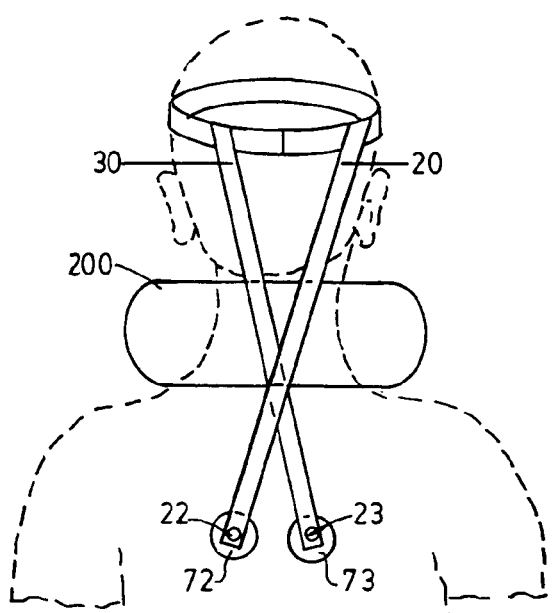
FIG. 7 is a rear perspective view of the device without an upper body garment portion but utilizing suction cups to attach the device to the user's back according to a third embodiment of the invention.

FIG. 7 is a rear perspective view according to a third embodiment of the invention which is made without use of a garment but utilizes suction cups to attach the device to the user's back. This alternative third embodiment has suction cups 72 and 73 as the anchoring system for head straps 20 and 30 allowing the lower end of head straps 20 and 30 to be attached to the back of the person using the device. Fasteners 22 and 23 (FIG. 7) located at the lower ends of head straps 20 and 30 respectively allow for fastening onto suction cups 72 and 73, which are adhered to the back of a user.

Figure 8:
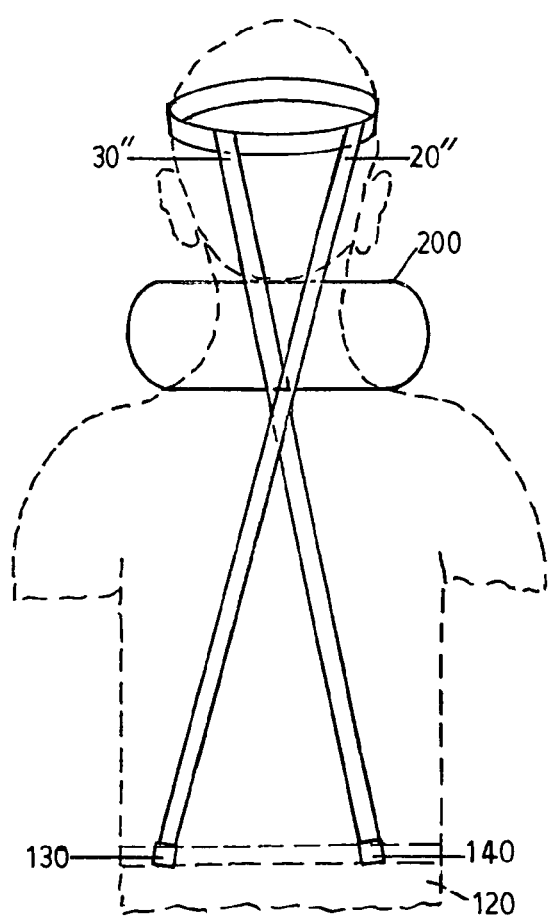
FIG. 8 is a rear perspective view of the device without an upper body garment portion and removably attached to the user's pajamas or underwear according to a fourth embodiment of the invention.

FIG. 8 is a rear perspective view of the invention device in a fourth embodiment shown without use of a garment 40 and illustrating head straps 20" and 30" removably attached to the user's pajamas, underwear or belt. In this fourth embodiment, head straps 20" and 30" connected at their lower ends via fasteners 130 and 140 to pants/shorts/pajamas/underwear 120 worn by the user in a manner compatible with the requirements of the invention. In this alternative fourth embodiment fasteners 130 and 140 are illustrated as clasps but may include hook and loop systems such as Velcro™ as well as other kinds of fasteners, such as buttons, adjustable buckle and strap arrangements, traditional hook and loop systems, snaps and any other fastening systems that can be used to join two pieces of material. Head straps 20" and 30"" may also be fastened to the belt of the user (not shown) when worn in a manner compatible with the requirements of the invention.

Figure 9:
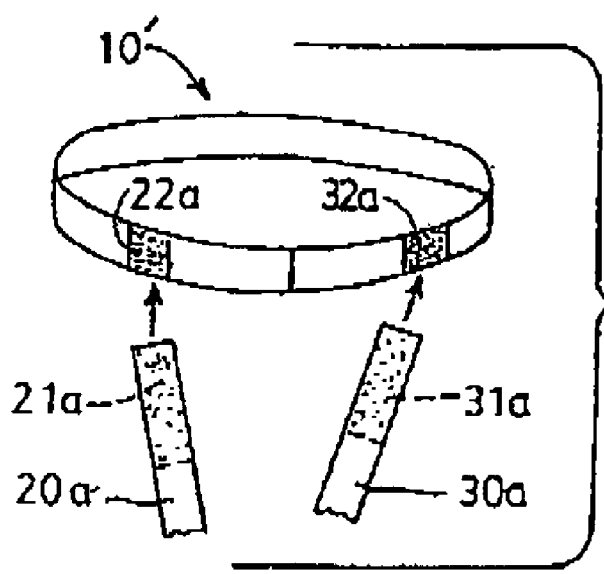
FIG. 9 is a fragmentary, exploded rear perspective view of the headband and adjustable straps of an embodiment of the invention.

FIG. 9 is a rear fragmentary, exploded perspective view of head band 10' and adjustable head straps 20a and 30a. Adjustable head strap 20a is attached to head band 10' using adjustable means 21a and 22a. Adjustable head strap 30a, is attached to head band 10' using adjustable means 31a and 32a. By way of example, the adjustable means for each strap could be hook and loop systems such as Velcro™, as shown here. Alternatively, other types of adjustable fasteners could be used.

Figure 10:
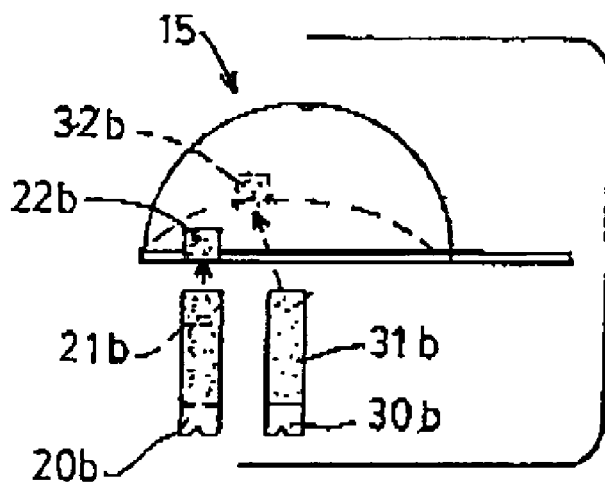
FIG. 10 is a fragmentary, exploded side elevation view of the head covering and adjustable straps of an embodiment of the invention.

FIG. 10 is a fragmentary, exploded side elevation view of head covering 15 and adjustable head straps 20b and 30b. Adjustable head strap 20b is attached to head covering 15 using adjustable means 21b and 22b. Adjustable head strap 30b, is attached to head covering 15 using adjustable means 31b and 32b. By way of example, the adjustable means for each strap could be hook and loop systems such as Velcro™, as shown here. Alternatively, other types of adjustable fasteners could be used.

The present embodiments of this device are thus to be considered in all respects as illustrative and not restrictive; all changes which come within the meaning and range of equivalency of the claims are intended to be embraced therein.

The invention claimed is:

1. A sleep apnea treatment device comprising:
   (a) a headband adapted by reason of its size and shape to fit around the head of a person using said device;
   (b) a garment adapted to being secured to the torso portion of said person consisting of a front section and a back section;
   (c) a first head strap affixed at one end to a first location on said headband;
   (d) a second head strap affixed at one end to a second location on said headband laterally spaced from said first location;
   (e) wherein said first and second head straps are each affixed at an opposite end to the back section of said garment in a manner adapted to provide tension in said head straps so as to cause said person's head to be tilted backwards and open said person's airway; and
   (f) wherein said first and second head straps are each of a length to tilt the head of said person using said device backwards and to open the person's airway.

2. The device according to claim 1, wherein said headband is made of an elastic material to accommodate varying head size.

3. The device according to claim 1, wherein said first and second head straps are affixed to said back section of said garment in a criss-cross manner.

4. The device according to claim 1, wherein said headband consists of a head cover.

5. The device according to claim 1, wherein said garment front section comprises first and second front panel sections joined to a common back portion forming said back section. said front and back sections in conjunction with a pair of shoulder straps forming a one-piece torso garment, and wherein each of said front panel sections is configured to have a fastener located at the front vertical edge of each of said front panel sections and constructed in a manner which allows for fastening of each front panel section to the respective opposite front panel section.

6. The device according to claim 5, wherein said fastener is a hook and loop system.

7. The device according to claim 5, wherein said fastener is a zipper.

8. The device according to claim 1, and including a pillow of size and dimension that can be placed behind the neck of a person using said device such that said pillow can be accommodated between said first and second head straps and the neck of said person.

9. The device according to claim 1, wherein said straps are attached at locations laterally opposed from each other on said headband.

10. The device according to claim 1, wherein said garment is in the form of a sports bra.

11. The device according to claim 1, wherein the first and second head straps are made of an elastic material.

12. The device according to claim 1, wherein the first and second head straps are adjustable in length.

* * * * *